US010160718B2

(12) United States Patent
Boone et al.

(10) Patent No.: US 10,160,718 B2
(45) Date of Patent: *Dec. 25, 2018

(54) METHODS OF MAKING COMPOUNDS HAVING ANTIDEGRADANT AND ANTIFATIGUE EFFICACY

(71) Applicant: Eastman Chemical Company, Kingsport, TN (US)

(72) Inventors: Matthew Allen Boone, Gray, TN (US); Donald L. Fields, Jr., Copley, OH (US); Frederick Ignatz-Hoover, Elyria, OH (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,298

(22) Filed: Jun. 9, 2017

(65) Prior Publication Data

US 2017/0275234 A1 Sep. 28, 2017

Related U.S. Application Data

(63) Continuation-in-part of application No. 15/371,257, filed on Dec. 7, 2016.

(60) Provisional application No. 62/270,909, filed on Dec. 22, 2015.

(51) Int. Cl.

| C07C 209/52 | (2006.01) |
|---|---|
| C07C 249/02 | (2006.01) |
| B60C 1/00 | (2006.01) |
| C08K 5/18 | (2006.01) |
| C10L 1/223 | (2006.01) |
| C10M 133/12 | (2006.01) |
| C07C 209/18 | (2006.01) |
| C07C 209/70 | (2006.01) |

(52) U.S. Cl.
CPC ............ *C07C 209/52* (2013.01); *B60C 1/00* (2013.01); *C07C 209/18* (2013.01); *C07C 209/70* (2013.01); *C07C 249/02* (2013.01); *C08K 5/18* (2013.01); *C10L 1/223* (2013.01); *C10M 133/12* (2013.01); C10L 2230/081 (2013.01); C10M 2215/067 (2013.01); C10N 2230/08 (2013.01); C10N 2230/10 (2013.01)

(58) Field of Classification Search
CPC .............. C10M 141/02; C10M 141/12; C10M 2201/041; C10M 2201/087; C10M 2201/084; C10M 2201/085; C10M 2201/102; C10M 2201/12; C10M 2207/122; C10M 2207/125; C10M 133/12; C10M 2215/067; C10N 2230/04; C10N 2230/02; C10N 2220/082; C10N 2240/404; C10N 2230/70; C10N 2230/10; C10N 2230/08; C07C 209/52; C07C 209/18; C07C 209/70; C07C 249/02; B60C 1/00; C08K 5/18; C10L 1/223; C10L 2230/081

See application file for complete search history.

(56) References Cited

U.S. PATENT DOCUMENTS

| 1,884,889 A | 10/1932 | Semon |
|---|---|---|
| 2,200,756 A | 5/1940 | Messer et al. |
| 2,905,654 A | 9/1959 | Ambelang |
| 3,398,193 A | 8/1968 | Wheeler |
| 4,627,929 A * | 12/1986 | Buysch ............... C10M 169/044 508/254 |
| 5,032,602 A | 7/1991 | Fey |
| 5,504,159 A | 4/1996 | Sturm et al. |
| 6,706,217 B2 | 3/2004 | Malz et al. |
| 7,563,929 B2 | 7/2009 | Hobbs et al. |
| 8,080,601 B2 | 12/2011 | Patil et al. |
| 8,080,689 B2 | 12/2011 | Kumar et al. |
| 8,833,417 B2 | 9/2014 | Da Silva et al. |
| 8,987,515 B2 | 3/2015 | Rowland |
| 2005/0159519 A1 | 7/2005 | Nakagome et al. |
| 2014/0316163 A1 | 10/2014 | Kumar et al. |
| 2015/0031810 A1 | 1/2015 | Araujo Da Silva et al. |
| 2017/0166727 A1 | 6/2017 | Saiki et al. |
| 2017/0320811 A1 | 11/2017 | Yan |

FOREIGN PATENT DOCUMENTS

| EP | 2952505 A1 | 12/2015 |
|---|---|---|
| GB | 835826 A | 5/1960 |
| KR | 20090100099 A | 9/2009 |
| KR | 1364781 | 2/2014 |
| SU | 250151 A1 | 12/1969 |
| WO | WO 2015/077635 A2 | 5/2015 |
| WO | WO 2015-178037 A1 | 11/2015 |
| WO | WO 2015-178038 A1 | 11/2015 |
| WO | WO 2015-178039 A1 | 11/2015 |
| WO | WO 2017-112440 A1 | 6/2017 |

OTHER PUBLICATIONS

Office Action dated Apr. 13, 2018 received in co-pending U.S. Appl. No. 15/618,288.
Office Action dated Apr. 19, 2018 received in co-pending U.S. Appl. No. 15/618,291.
Bitsi et al., N-Alkylation d'amines en Catalyse Homogene. Sythese de monoet de daimines Cycliques, Sep. 19, 1989, Journal of Oranometallic Chemistry, vol. 373, Issue 3 (Year: 1989).
Copending U.S. Appl. No. 15/371,257, filed Dec. 7, 2016, Boone et al.
Oberster, A.E. et.al Canadian Journal of Chemistry 1966, 45, 195-201.
Guillena, et.al. Chem. Rev. 2010, 110, 1611.

(Continued)

*Primary Examiner* — Taiwo Oladapo
(74) *Attorney, Agent, or Firm* — Michael Carrier

(57) ABSTRACT

A method of making antidegradant compounds is disclosed, in which a p-phenylenediamine is reacted with an alpha-hydroxy carbonyl compound to thereby obtain an enediamine, which is reduced to thereby obtain a mixture comprising the antidegradant compound.

11 Claims, No Drawings

(56) References Cited

OTHER PUBLICATIONS

Centre for Chemical Substances and Preparations, Slovaki; "Justification Document for the Selection of a Corap Substance" http://echa.europa.eu/documents/10162/9801478/corap_justification_448-020-2_sk_en.pdf (Accessed May 11, 2015).
HallStar. "The Use of Antiozonants in Rubber Compounding" http://www.hallstar.com/techdocs/ANTIOZO.pdf (Accessed May 11, 2015).
PCT International Search Report and Written Opinion dated Mar. 9, 2017 for International Application No. PCT/US2016/066085.
Copending U.S. Appl. No. 15/618,281, filed Jun. 9, 2017, Boone et al.
Copending U.S. Appl. No. 15/618,288, filed Jun. 9, 2017, Boone et al.
Copending U.S. Appl. No. 15/618,291, filed Jun. 9, 2017, Boone et al.
Copending U.S. Appl. No. 15/618,301, filed Jun. 9, 2017, Boone et al.
PCT International Search Report and Written Opinion dated Sep. 13, 2018 for International Application No. PCT/US2018/033095.
Guangxun et al., "Investigation and application of amphoteric alpha-amino aldehyde: an in situ generated species based on Heyns rearrangement", Organic Letters, vol. 18, No. 18, Aug. 30, 2016, pp. 4526-4529.
Office Action dated Oct. 5, 2018 received in co-pending U.S. Appl. No. 15/618,288.
Office Action dated Sep. 19, 2018 received in co-pending U.S. Appl. No. 16/103,080.
PCT International Search Report and Written Opinion dated Aug. 28, 2018 for International Application No. PCT/US2018/033107.
PCT International Search Report and Written Opinion dated Sep. 11, 2018 for International Application No. PCT/US2018/033104.
Office Action dated Apr. 25, 2018 received in co-pending U.S. Appl. No. 15/371,257.
Office Action dated Apr. 25, 2018 received in co-pending U.S. Appl. No. 15/618,281.
Office Action dated Apr. 27, 2018 received in co-pending U.S. Appl. No. 15/618,301.
Copending U.S. Appl. No. 16/103,080, filed Aug. 14, 2018, Boone et al.
PCT International Search Report and Written Opinion dated Aug. 13, 2018 for International Application No. PCT/US2018/033101.
PCT International Search Report and Written Opinion dated Aug. 21, 2018 for International Application No. PCT/US2018/033106.

* cited by examiner

METHODS OF MAKING COMPOUNDS HAVING ANTIDEGRADANT AND ANTIFATIGUE EFFICACY

RELATED APPLICATIONS

This continuation-in-part application claims the priority benefit of U.S. Nonprovisional patent application Ser. No. 15/371,257 filed Dec. 7, 2016, which in turn claims priority to U.S. Provisional Patent Application Ser. No. 62/270,909, titled "COMPOUNDS WITH ANTIDEGRADANT AND ANTIFATIGUE EFFICACY AND COMPOSITIONS INCLUDING SAID COMPOUNDS," filed Dec. 22, 2015, the entire disclosures of which are incorporated herein by reference.

FIELD OF THE INVENTION

The present invention relates generally to methods of making compounds with antidegradant and antifatigue efficacy that are useful as an additive for vulcanized rubber articles, vulcanizable elastomeric formulations, lubricants, fuels, fuel additives and other compositions which require such efficacy or in compositions which are themselves useful as compositions to impart such efficacy.

BACKGROUND OF THE INVENTION

Many materials such as plastics, elastomers, lubricants, cosmetics and petroleum products (such as hydraulic fluids, oils, fuels and oil/fuel additives for automotive and aviation applications) are prone to degradation upon prolonged exposure to light, heat, oxygen, ozone, repetitive mechanical actions and the like. Accordingly, compounds and compositions demonstrating antidegradant efficacy are well known in the art. For example, U.S. Pat. No. 8,987,515 discloses an aromatic polyamine useful in inhibiting oxidative degradation particularly in lubricant compositions. U.S. Patent Application Publication number 2014/0316163 discloses antioxidant macromolecules with purported improved solubility in many commercially available oils and lubricants.

Antidegradants useful in the manufacture of articles formed from elastomers, plastics and the like require a very specific combination of qualities that can be difficult to achieve. While the antidegradants must obviously have commercially acceptable efficacy, they must also exhibit that efficacy over prolonged periods of time associated with use of the article, particularly at exposed surfaces of the article where degradation from environmental factors such as light, oxygen and ozone primarily occurs. Just as important to the protection of surface exposed components, efficacy in protecting imbedded components of composite materials from the effects of oxidative aging and repetitive mechanical action are critically important. The antidegradants must achieve these results while not negatively impacting other additives' efficacy or desirable characteristics in the final article. Further, antidegradants which provide or improve the mechanical fatigue life after an article has been in service, aged oxidatively or by exposure to ozone are highly valued since these will inherently improve the useful mechanical service life of article. Consequently, elastomeric articles which undergo repeated mechanical flexure, extension, or compression during service would greatly benefit from such a discovery.

Articles formed from general purpose elastomers such as natural rubber, in particular tires, are especially prone to degradation from both oxygen and ozone. As discussed in U.S. Pat. No. 2,905,654, the effect on rubber from degradation by oxygen is different from the effect from degradation from ozone; however, both effects can be detrimental to tire performance, appearance and life expectancy. Fatigue and crack propagation are also issues of specific concern, in particular for steel belt edge areas and tire sidewalls which are subject to significant stresses and stretching forces while flexed whether inflated, partially inflated and throughout the service life of the tire. U.S. Pat. No. 8,833,417 describes an antioxidant system that purportedly increases long-term resistance to fatigue and crack propagation over the known antioxidants discussed immediately below.

Materials with antidegradant efficacy are well known in the art for use in tire applications and are commercially available. For example, N,N'-disubstituted-paraphenylenediamines such as those sold by Eastman Chemical Company under the trademark Santoflex® are generally favored by many tire manufacturers for this purpose. EP Pat. Appln. Publn. No. EP 3 147 321 A1 discloses rubber compositions, tires, amine compounds, and anti-aging agents, and in particular, a rubber composition that is said to be suitable for use in tread rubber or sidewall rubber of a tire. As governmental regulation, market needs and customer expectations push the rubber industry toward lighter weight tires to enhance fuel efficiency and conserve natural resource feedstocks, a continuing need nonetheless exists for improved antidegradants, and methods of making them, that exhibit (i) multiple efficacies against fatigue, crack propagation and the various mechanisms of degradation; (ii) increased efficacy, especially at lower concentrations and (iii) longer efficacy periods when compared to current commercial materials.

SUMMARY OF THE INVENTION

In one aspect, the present invention relates to methods of making antidegradant compounds, and mixtures containing them, that correspond to formula I as set out below and as further described herein. In this aspect, a p-phenylenediamine corresponding to formula IV:

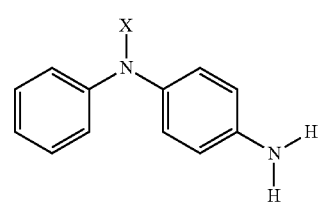

IV wherein each X is independently selected from the group consisting of alkyl, aryl, alkylaryl groups and hydrogen; or wherein each X is independently hydrogen or methyl;

is reacted with an alpha-hydroxy carbonyl corresponding to formula II:

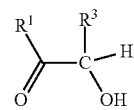

II wherein $R^1$ and $R^3$ are each independently selected from:
(a) the group consisting of alkyl, aryl, alkylaryl groups and hydrogen; or (b) the group consisting of butyl, propyl, ethyl, methyl or hydrogen; and wherein $R^1$ and $R^3$ may optionally be bridged by a polymethylene group;

to thereby obtain an enediamine corresponding to formula III:

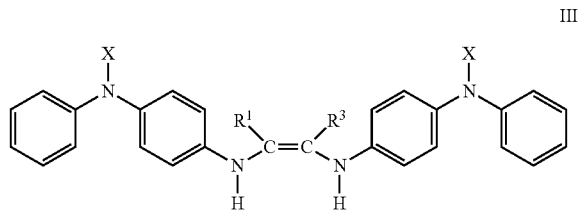

wherein the variables are as described, for example, with respect to formulas IV and II above. In formula III, although the structure depicted suggests a Z conformation, we do not intend to exclude the possibility that substantial or even major amounts of the E conformation are present. The invention thus relates to the Z conformation, the E conformation, and any mixtures of the two conformations.

The enediamine corresponding to formula III may then be reduced or hydrogenated to obtain a mixture that includes the antidegradant compound according to formula I:

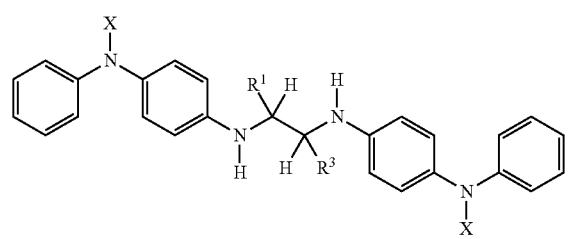

wherein each X is independently selected from the group consisting of alkyl, aryl, alkylaryl groups and hydrogen; or wherein each X is independently hydrogen or methyl;
wherein $R^1$ and $R^3$ are each independently selected from:
(a) the group consisting of alkyl, aryl, alkylaryl groups and hydrogen; or (b) the group consisting of butyl, propyl, ethyl, methyl or hydrogen; and wherein $R^1$ and $R^3$ may optionally be bridged by a polymethylene group;

In a second aspect, the present invention relates to compositions, and methods of making them, that include a compound represented by formula I as set out above. In a further aspect, the present invention is directed to antidegradant compositions and mixtures that include the antidegradant compounds of the present invention.

In a further aspect, the present invention is directed to an antidegradant composition including the compound of the present invention.

In another aspect, the present invention is directed to a lubricant composition including the compound of the present invention.

In yet another aspect, the present invention is directed to a vulcanizable elastomeric formulation including the compound of the present invention.

In still another aspect, the present invention is directed to a vulcanized elastomeric rubber article with at least one component formed from a vulcanizable elastomeric formulation of the present invention.

The compounds of the present invention have surprisingly demonstrated antidegradant and antifatigue agent efficacies and accordingly are particularly useful in imparting resistance to crack propagation, degradation and the many manifestations thereof in a variety of applications. When utilized as a component in vulcanizable elastomeric formulations for forming vulcanized rubber articles, and specifically in vehicle tires and their components, the compounds of the present invention have demonstrated a particularly desirable and surprising combined efficacy against oxidative degradation, ozonative degradation and resistance against fatigue and crack propagation that is superior to the combination heretofore achieved by prior art materials. Further advantages and areas of applicability will become apparent from the description provided herein. It should be understood that the description and specific examples are intended for purposes of illustration only and are not intended to limit the spirit and scope of the present invention.

DETAILED DESCRIPTION

As utilized herein, the following terms or phrases are defined as follows:

"Antidegradant" refers to a material that inhibits degradation (as caused by for example, through heat, light, oxidation, and/or ozonation), or manifestations thereof, of a composition, formulation or article to which it is added or applied.

"Antifatigue agent" refers to a material that improves the flex fatigue resistance of a composition, formulation or article to which it is added or applied after a period of in-service application time whereby the composition, formulation or article is subjected to thermal, oxidative, ozone and mechanical degradative forces.

"Antioxidant" refers to a material that inhibits oxidative degradation of a composition, formulation or article to which it is added or applied.

"Antiozonant" refers to a material that inhibits ozone exposure degradation of a composition, formulation or article to which it is added or applied.

"Elastomer" means any polymer which after vulcanization (or crosslinking) and at room temperature can be stretched under low stress to at least twice its original length and, upon immediate release of the stress, will return with force to approximately its original length, including without limitation rubber.

"Vulcanizable Elastomeric Formulation" means a composition that includes an elastomer and that is capable of vulcanization when placed under vulcanization conditions.

Non-limiting examples of the compound of the present invention include N,N'-(ethane-1,2-diyl)bis(N-phenylbenzene-1,4-diamine) and N,N'-(butane-2,3-diyl)bis(N-phenylbenzene-1,4-diamine). These are represented schematically as follows, each with a reference to the corresponding written example(s) below that describes a method for manufacture:

Example 2

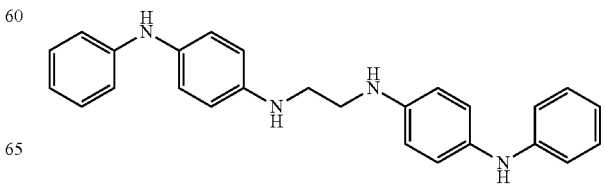

Example 4

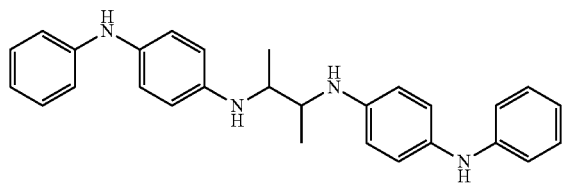

Preferred examples of the compounds of the present invention according to formula I thus include N,N'-(ethane-1,2-diyl)bis(N-phenylbenzene-1,4-diamine) and N,N'-(butane-2,3-diyl)bis(N-phenylbenzene-1,4-diamine), as depicted above.

In one aspect, the present invention thus relates to methods of making antidegradant compounds, and mixtures containing them, that correspond to formula I as set out above and as further described herein. In this aspect, a p-phenylenediamine corresponding to formula IV:

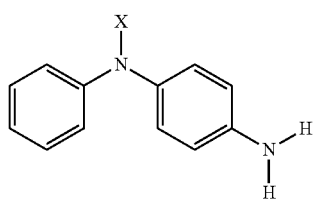

IV wherein each X is independently selected from the group consisting of alkyl, aryl, alkylaryl groups and hydrogen; or wherein each X is independently hydrogen or methyl;

is reacted with an alpha-hydroxy carbonyl corresponding to formula II:

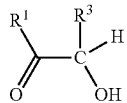

II wherein $R^1$ and $R^3$ are each independently selected from: (a) the group consisting of alkyl, aryl, alkylaryl groups and hydrogen; or (b) the group consisting of butyl, propyl, ethyl, methyl or hydrogen; and wherein $R^1$ and $R^3$ may optionally be bridged by a polymethylene group;

to thereby obtain a enediamine corresponding to formula III:

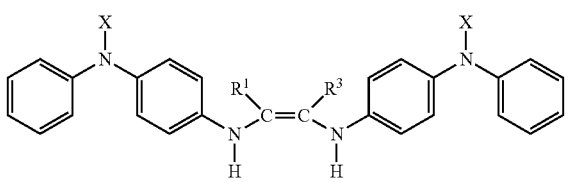

III wherein the variables are as described with respect to formulas IV and II above.

The enediamine corresponding to formula III may then be reduced or hydrogenated to obtain a mixture that includes the antidegradant compound according to formula I:

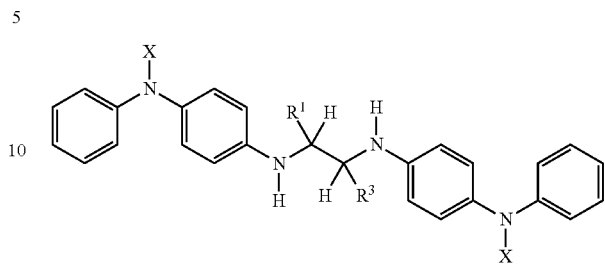

I wherein each X is independently selected from the group consisting of alkyl, aryl, alkylaryl groups and hydrogen; or wherein each X is independently hydrogen or methyl;

wherein $R^1$ and $R^3$ are each independently selected from: (a) the group consisting of alkyl, aryl, alkylaryl groups and hydrogen; or (b) the group consisting of butyl, propyl, ethyl, methyl or hydrogen; and wherein $R^1$ and $R^3$ may optionally be bridged by a polymethylene group.

Suitable p-phenylenediamines useful according to the invention that correspond to formula IV include those in which each X is independently selected from alkyl, aryl, alkylaryl groups and hydrogen; and especially those in which each X is independently hydrogen or methyl, and especially 4-aminoparaphenylene diamine.

Suitable alpha-hydroxy carbonyls useful according to the invention that correspond to formula II include those in which $R^1$ and $R^3$ are each independently selected from the group consisting of butyl, propyl, ethyl, methyl or hydrogen; and especially methyl or hydrogen. Suitable alpha-hydroxy carbonyls also include those in which $R^1$ and $R^3$ are bridged by a polymethylene group to form a cycloalkyl. Examples of suitable alpha-hydroxy carbonyls include acetoin, alphahydroxyacetone (acetol) and benzoin. Those skilled in the art would readily appreciate that a benzoin-type condensation reaction may be used to produce an array of alphahydroxycarbonyl compounds that may be useful according to the invention, whether or not the resulting compound is aromatic.

The enediamines of formula III thereby obtained include especially those in which each X is independently hydrogen or methyl; and in which $R^1$ and $R^3$ are each selected from ethyl, methyl or hydrogen; and those in which $R^1$ and $R^3$ are bridged by a polymethylene group to form a cycloalkyl group.

The antidegradant compounds of the invention corresponding to formula I as described herein are obtained by reduction or hydrogenation of the enediamines corresponding to formula III, as described hereinafter.

According to the invention, enediamines represented by formula III can be prepared by contacting a p-phenylenediamine compound represented by formula I with an alpha-hydroxy carbonyl compound represented by formula II in the presence of a solvent and an acid catalyst. Preferred p-phenylenediamines include those in which X corresponds to methyl or hydrogen, and especially hydrogen, that is, 4-aminodiphenylamine (4-ADPA). Preferred diols according to formula II include those in which $R^1$ and $R^3$ are each selected from the group consisting of butyl, propyl, ethyl, methyl, or hydrogen, and especially methyl.

In preparing the enediamines of formula III according to the invention, suitable solvents include, but are not limited to, methanol, ethanol, isopropanol, and n-butanol, cyclohexane, toluene, heptane, glycol ethers, methyl acetate, ethyl acetate, butyl acetate, and mixtures thereof. Examples of acid catalysts that may be useful to prepare the enediamines include, but are not limited to, formic acid, acetic acid, propionic acid, p-toluenesulfonic acid, camphorsulfonic acid, HCl, $H_2SO_4$, $H_3PO_4$ and solid-supported acidic resins. The temperature of the reaction may be carried out, for example, at temperatures from about 0° C. to about 100° C., or from 5° C. to 75° C., or from 40° C. to 60° C.

According to the invention, an antidegradant compound represented by formula I can be synthesized by reduction of precursor enediamine compounds represented by formula III as just described. This reduction may be carried out in the presence of a solvent with a homogeneous or heterogeneous metal catalyst, in the presence of hydrogen gas or formic acid or a formic acid salt.

The solvent can be selected from those commonly used in hydrogenation or transfer hydrogenation reactions. Examples of such solvents include, but are not limited to, methanol, ethanol, isopropanol, butanol, cyclohexane, ethylene glycol, tert-butyl methyl ether, tetrahydrofuran, formic acid, acetic acid, dimethylformamide, dimethylacetamide, N-methylpyrrolidone, N-butylpyrrolidone, methyl acetate, ethyl acetate, butyl acetate, diethylene glycol monobutyl ether, methyl isobutyl ketone. These solvents can be used individually or in combinations as a mixture. The amount of solvent used may be based on the amount of alpha-hydroxy carbonyl represented by formula II, such that the weight % solvent ranges from about 1 to about 75%, or from 20 to 40%, based on the amount of alpha-hydroxy carbonyl present.

Examples of metal catalysts that can be used for hydrogenation or reduction include but are not limited to palladium on carbon, palladium on alumina, platinum on carbon, sulfided platinum on carbon, platinum on alumina, platinum on silica, platinum oxide, Raney nickel, Raney cobalt, ruthenium on carbon, ruthenium on alumina, and a homogenous metal catalyst such as chlorotris(triphenylphosphine) rhodium(I) (Wilkinson's catalyst).

The amount of catalyst used may be based on the amount of alpha-hydroxy carbonyl present, such that the weight % catalyst ranges from about 0.005 to about 20% by weight of active catalyst, excluding water content, based on the amount of alpha-hydroxy carbonyl present.

The hydrogen pressure used in the catalytic hydrogenation can range from about atmospheric pressure to about 2,000 psig, or from atmospheric to 500 psig, or at approximately atmospheric pressure. Alternatively, formic acid or formic acid salts can serve as the hydrogen source for the reduction.

The temperature of the reaction can range from ambient temperature up to 250° C.

Each of the above parameters may affect the reaction kinetics, conversion, and selectivity. It is preferred that reaction conditions are selected such that time required for completion is from 30 minutes to 100 hrs.

According to the invention, the processes of the invention may also be used to prepare mixtures of antidegradant compounds. Thus, a mixture of the disclosed antidegradant products of the invention and an alky, aryl p-phenylenediamine such as 6PPD or IPPD can be produced by using a ketone such as MIBK or acetone, respectively, as the hydrogenation reaction solvent. Such a product may be desirable to produce an antidegradant product mixture having different migration characteristics. The reaction proceeds with hydrogenation of the diimine to form the diamine. Concomitantly, the ketone solvent will react with any residual 4-ADPA in the diimine starting material, any added additional 4-ADPA and/or any 4-ADPA from hydrolysis of the di-imine to form the alkyl,aryl p-phenylenediamine.

The compounds of the present invention may also be prepared from a polyalcohol starting material through a hydrogen autotransfer procedure using a homogenous or heterogeneous catalyst (see e.g. Guillena, et. al. *Chem. Rev.* 2010, 110, 1611 for a general description of the mechanism). The compounds of interest can also be prepared from a polycarbonyl starting material using a heterogeneous transition metal catalyst in the presence of hydrogen.

Precursors for compounds of the present invention, the compounds of the present invention and methods for their manufacture are illustrated by the following examples, which are not intended in to any limit the spirit or scope of the present invention.

EXAMPLE 1

Preparation of Precursor (N,N',N,N')-N,N'-(ethane-1,2-diylidene)bis(N-phenylbenzene-1,4-diamine)

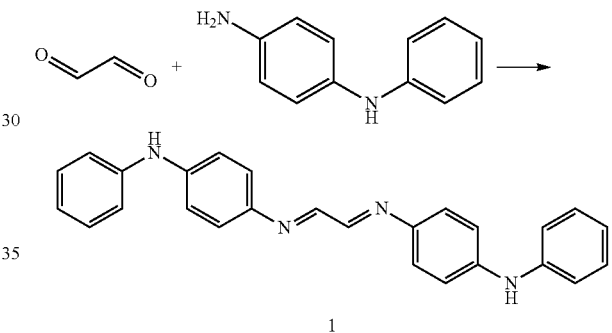

In a 3-neck 1 L round-bottom flask with overhead stirrer, 4-ADPA (127 g, 689 mmol) was dissolved in EtOH (200 proof, 363 mL). In a separate beaker, glyoxal (40% in water, 50 g, 345 mmol) was added to a mixture of EtOH:water (1:1, 100 mL). The glyoxal solution was then added drop wise to the reaction mixture over a 50 minute period—a red solid began to form during the addition. The mixture was stirred for an additional 20 minutes, after which water (150 mL) was added all at once to further precipite the dark red solid. The slurry was stirred overnight. After recovering the solid by filtration and washing with additional water, the red solid was placed in a 50° C. vacuum oven (with nitrogen sweep) overnight (131.57 g, 98% yield). $^1$H NMR (300 MHz, DMSO-d6) δ 8.49 (bs, 2H), 8.47 (s, 2H), 7.38 (m, 4H), 7.31-7.28 (m, 4H), 7.16-7.11 (m, 8H), 6.92-6.89 (m, 2H).

EXAMPLE 2

Preparation of N,N'-(ethane-1,2-diyl)bis(N-phenylbenzene-1,4-diamine)

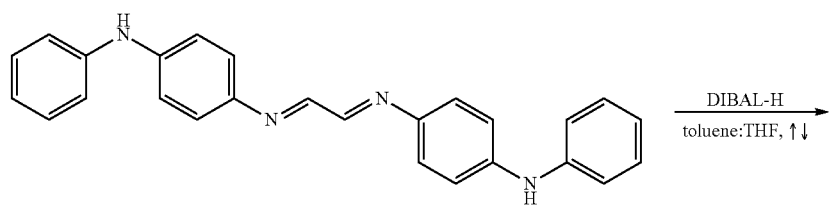

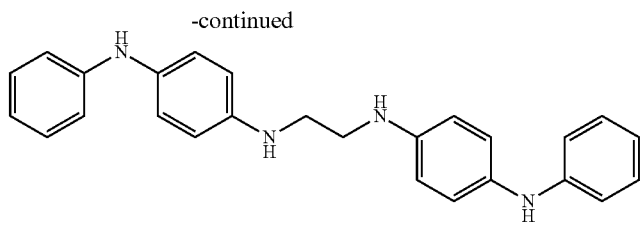

2

DIBAL-H (122 g, 25 wt. % in toluene) was slowly cannulated into a 1 L round-bottom flask that contained THF (102 mL). Then the di-imine 1 (20.0 g, 50.2 mmol) was carefully added at ambient temperature. After the addition was complete, the mixture was heated to 60° C. and allowed to react for 19.25 hours. Then the reaction was cooled using an ice-water bath to ca. 5-10° C., at which point a saturated solution of NaK tartrate was added drop wise until the reaction mixture formed a gel. At that point, 250 mL of the NaK tartrate solution was quickly added, followed by 500 mL of EtOAc. The biphasic mixture was vigorously stirred overnight. The mixture was then transferred to a 1-L separatory funnel, and the layers were then separated. The organics were dried with $Na_2SO_4$. The mixture was then filtered through a short plug of silica gel, and the cake was rinsed with a small amount of EtOAc and THF. The product was isolated as a light brown powder (17.3 g, 86% yield). ICP analysis: 86 ppm aluminum. Tm=167.09° C. $^1$H NMR (500 MHz, DMSO-d6) δ7.50 (bs, 2H), 7.10 (m, 4H), 6.91 (m, 4H), 6.79 (m, 4H), 6.62-6.58 (m, 6H), 5.35 (bs, 2H), 3.21 (m, 4H).

EXAMPLE 3

Alternative preparation of N,N'-(ethane-1,2-diyl)bis(N-phenylbenzene-1,4-diamine)

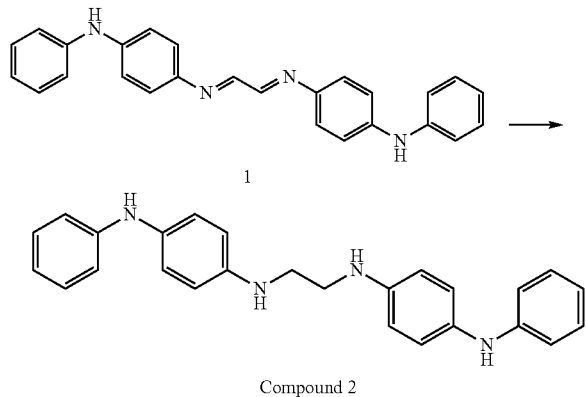

Compound 2

Procedure: 20 g of water-wet Raney Ni slurry was transferred to a Parr bottle. Then 400 g of dimethylformamide (DMF) and 200 g of EtOH were added. 200 g of bis-imine 1 was added to the catalyst/solvent mixture. The bottle was placed in a Parr shaker apparatus and was purged with nitrogen three times. The vessel was purged with $H_2$ gas three times and then pressurized to 40 psig. Agitation was initiated, and the contents were heated to an internal set point of 48° C. Once the reaction was at temperature, the $H_2$ pressure was adjusted to 50 psig. The reaction was agitated for 2.5 hrs, and then allowed to cool to ambient temp over 1 hr. The catalyst was clarified by passing the mixture through a plug of celite, using a minimal amount of DMF/EtOH (110 g DMF, 140 g of EtOH) to rinse the bottle and cake. The homogeneous mixture was transferred to a 1 L round-bottom flask with magnetic stir bar. 750 g of water was added via pressure-equalizing dropping funnel over a 40 minute period with vigorous stirring. The precipitated solids were filtered through a 1 micron glass fiber disc and washed with 2.5 L of water. The solids were transferred to a 1 L Erlenmeyer flask and stirred with a stir bar in ca. 750 mL of $H_2O$ for 4 hrs. The solids were once again filtered and washed with additional $H_2O$. The brown solid was placed in a 60° C. vacuum oven with $N_2$ sweep and allowed to dry overnight. Isolated yield: 179 g, 90% yield, 99% selectivity. Tm=167.09° C. $^1$H NMR (500 MHz, DMSO-d6) δ 7.50 (bs, 2H), 7.10 (m, 4H), 6.91 (m, 4H), 6.79 (m, 4H), 6.62-6.58 (m, 6H), 5.35 (bs, 2H), 3.21 (m, 4H).

EXAMPLE 4

Preparation of Precursor (N,N')-N,N'-(butane-2,3-diylidene)bis(N-phenylbenzene-1,4-diamine) [which name do we want to use for this molecule?]

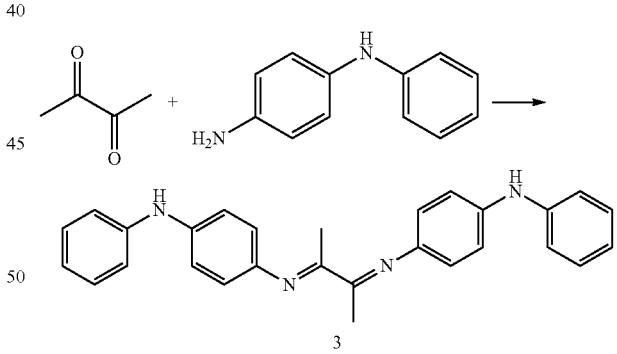

3

In a 3-neck 1 L round-bottom flask with overhead stirrer, 4-ADPA (128 g, 689 mmol) was dissolved in EtOH (200 proof, 375 mL). Biacetyl (30.0 g, 348 mmol) was added drop wise via pressure-equalizing addition funnel over a 20 minute period. After 13 hours, heptane (375 mL) was added in ca. 50 mL portions over a 40 minute period (slow addition of heptane helped to reduce clumping). The mixture was vigorously stirred for 15 minutes and then filtered. The solids were washed with additional heptane and then dried in a 50° C. vacuum oven with nitrogen sweep (67.45 g, 46% yield). $^1$H NMR (500 MHz, DMSO-d6) δ 8.13 (bs, 2H), 7.24 (m, 4H), 7.12 (m, 4H), 7.06 (m, 4H), 6.82-6.79 (m, 6H) 2.17 (s, 6H).

EXAMPLE 5

Alternative Preparation of 4,4-(((2E,3E)-butane-2,3-diylidene)bis(azaneylylidene))bis(N-phenylaniline) [which name?]

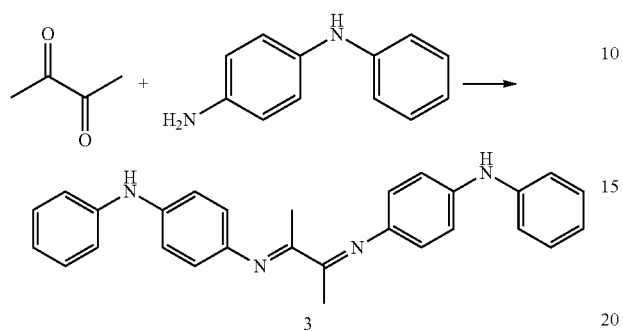

Procedure: In a 3-neck 3 L round-bottom flask with overhead stirrer, 4-ADPA (690 g, 3.8 mol) was dissolved in 1800 g of EtOH and 780 g of heptane. 5.02 g of phosphoric acid (85%) was then added. Biacetyl (150 g, 1.7 mol) was added drop wise via pressure-equalizing addition funnel over a 5 minute period. The mixture was heated to 50° C. After 24 hours, the reaction was cooled to ambient temperature. The yellow-green solids were filtered washed with 1 L of saturated NaHCO$_3$, followed by two, 1 L washings with water. The filter cake was washed with 1 L of isopropanol and then 1 L of heptane. The solids were dried in a 50° C. vacuum oven with nitrogen sweep (569 g, 78% yield). $^1$H NMR (500 MHz, DMSO-d6) δ 8.13 (bs, 2H), 7.24 (m, 4H), 7.12 (m, 4H), 7.06 (m, 4H), 6.82-6.79 (m, 6H) 2.17 (s, 6H).

EXAMPLE 6

Preparation of N,N'-(butane-2,3-diyl)bis(N-phenyl-benzene-1,4-diamine)

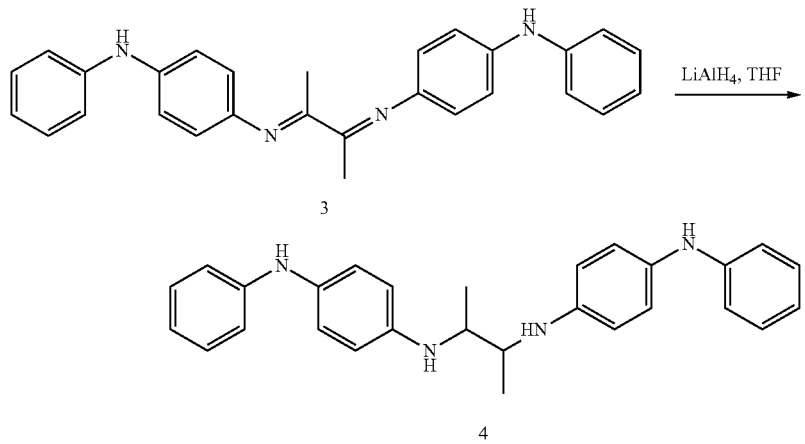

LiAlH$_4$ (7.40 g, 1995 mmol) was carefully added to THF (162 mL) in a 1 L round-bottom flask. Di-imine 3 (20.4 g, 48.7 mmol) was carefully added to the solution. After the addition was complete, the reaction was refluxed for 4 hrs. After this time, the mixture was cooled using an ice water bath and then carefully quenched by the drop wise addition of water (25 mL) followed by drop wise addition of 15% NaOH (50 mL). An additional 150 mL of water was added to the mixture and then stirred overnight. After filtration, the brown liquid was concentrated under reduced pressure using a rotary evaporator. The resulting brown solid was washed with heptane and then dried in a 45° C. vacuum oven with nitrogen sweep (16.5 g, 80% yield). ($^1$H NMR indicated a mixture of the meso compound and corresponding isomer). Tm=175.02° C. $^1$H NMR (300 MHz, CDCl3) δ 7.24 (m, 4H), 7.00 (m, 4H), 6.85-6.75 (m, 6H), 6.70-6.55 (m, 4H), 5.40 (bs, 2H), 3.75-3.50 (m, 4H), 1.25 (m, 6H).

EXAMPLE 7

Alternative Preparation of N,N'-(butane-2,3-diyl)bis(N-phenylbenzene-1,4-diamine)

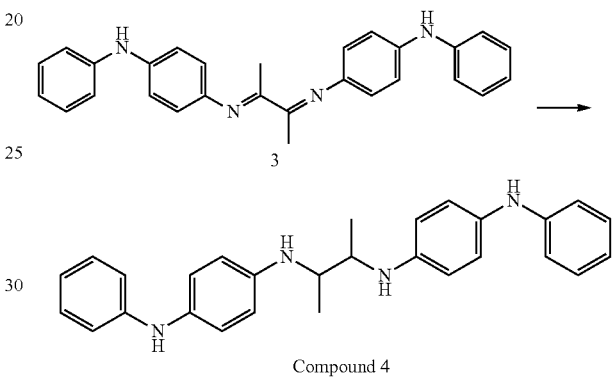

Procedure: 2.5 g of 5% Pt—C (50% water wet) was transferred to a Parr bottle. Then 75 g of EtOAc was added 25 g of bis-imine 3 was added to the catalyst/solvent mixture. The bottle was placed in a Parr shaker apparatus and was purged with nitrogen three times. The vessel was purged with H$_2$ gas three times and then pressurized to 50 psig. Agitation was initiated. The reaction was agitated for 3 hrs. The catalyst was clarified by passing the mixture through a plug of celite. The volatiles were removed under reduced pressure using a rotary evaporator. The product was isolated a viscous liquid that solidified upon cooling to ambient temperature. Recovered 22 g, 86% yield, 99% selectivity. (¹H NMR indicated a mixture of the meso compound and corresponding isomer). ¹H NMR (500 MHz, DMSO-d6) δ 7.49 (bs, 4H, major isomer), 7.47 (bs, 2H, minor isomer), 7.10 (m, 4H), 6.92-6.86 (m, 4H), 6.79 (m, 4H), 6.64-6.55 (m, 6H), 5.07 (d, 2H, major isomer), 4.92 (d, 2H, minor isomer), 3.51 (m, 4H), 1.15 (d, 6H, major isomer), 1.11 (d, 6H, minor isomer).

EXAMPLE 8

Alternative Preparation of N,N'-(butane-2,3-diyl)bis(N-phenylbenzene-1,4-diamine)

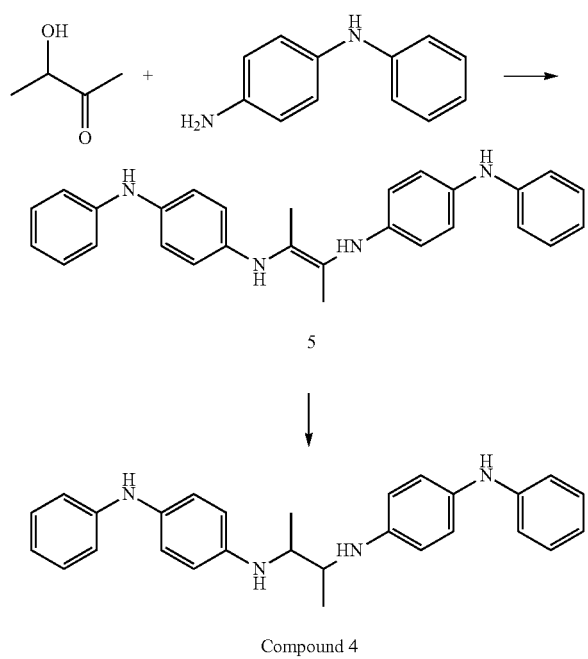

Procedure: Acetoin (5.0 g, 57 mmol) was transferred to a 250 mL round-bottom flask with magnetic stir bar. Then 4-ADPA (21 g, 110 mmol) was added to the flask followed by the addition of EtOH (75 g). Amberlyst 15 (dry, 500 mg) was added to the mixture, which was then allowed to stir for 70 hrs at 50° C. The mix was then allowed to cool to ambient temperature and stirred for an additional 5 hrs. The yellow solids/catalyst were filtered and washed with some heptane. NMR analysis of intermediate indicated the desired ene-diamine. ¹H NMR (500 MHz, DMSO-d6) δ 8.13 (bs, 2H), 7.24 (m, 4H), 7.12 (m, 4H), 7.07 (m, 4H), 6.81 (m, 6H), 2.17 (s, 6H). 3.5 g of ene-diamine/catalyst mixture and 500 mg of 5% Pt—C (50% water wet) were transferred to a Parr bottle. Then 50 g of EtOAc and 25 g of EtOH were added. The bottle was placed in a Parr shaker apparatus and was purged with nitrogen three times. The vessel was purged with H₂ gas three times and then pressurized to 50 psig. Agitation was initiated, and the reaction was agitated for 2.5 hrs. The catalyst was clarified by passing the mixture through a plug of celite. The volatiles were removed under reduced pressure using a rotary evaporator. (¹H NMR indicated a mixture of the meso compound and corresponding isomer). ¹H NMR (500 MHz, DMSO-d6) δ 7.49 (bs, 4H, major isomer), 7.47 (bs, 2H, minor isomer), 7.10 (m, 4H), 6.92-6.86 (m, 4H), 6.79 (m, 4H), 6.64-6.55 (m, 6H), 5.07 (d, 2H, major isomer), 4.92 (d, 2H, minor isomer), 3.51 (m, 4H), 1.15 (d, 6H, major isomer), 1.11 (d, 6H, minor isomer).

EXAMPLE 9

Preparation of a mixture of N,N'-(ethane-1,2-diyl)bis(N-phenylbenzene-1,4-diamine) Compound 2 and N-1,3-dimethylbutyl-N'-phenyl-p-phenylenediamine (6PPD)

A mixture of 3.0 g of the bis-imine 1, 75 mL of methyl isobutyketone (MIBK) and 0.10 g of 3% Pt—C (sulfided) catalyst was charged to a 300 mL Parr autoclave. The system was purged three times with nitrogen by pressurizing to 100 psig and releasing. After the nitrogen purge, the system was pressurized to 400 psig with hydrogen and heated to 125° C. with agitation rate at 1800 rpm. The hydrogen pressure was maintained at 400 psig throughout the reaction. The system was reacted for 5.5 hrs at which time no further hydrogen consumption could be detected. The autoclave was cooled to room temperature. HPLC-MS analysis revealed the product mixture to contain approximately equal amounts of the diamine product (compound 2) and 6PPD.

EXAMPLE 10

Preparation of N,N'-(octane-1,8-diyl)bis(N-phenylbenzene-1,4-diamine)

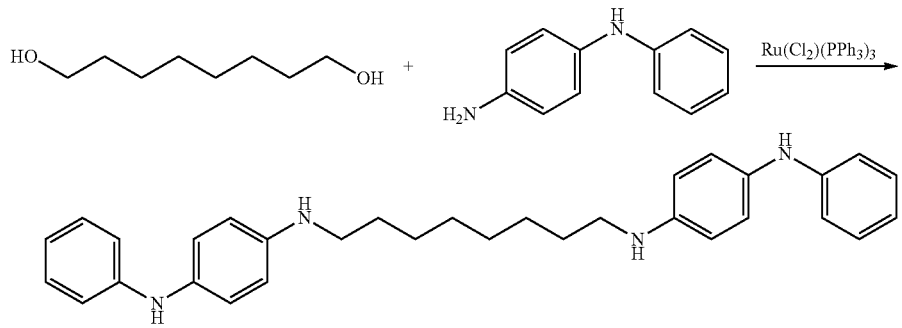

Octane-1,8-diol (10.0 g, 68.4 mmol), 4-ADPA (25.2 g, 137 mmol), and RuCl2(PPh3)3 (3.28 g, 3.42 mmol) were transferred to a 250 mL thick-walled, round bottom flask with a Teflon screw-top. A magnetic stir bar was added. The flask was sealed and then heated to 135° C. After 2.5 hours at this temperature, the reaction was then cooled to ambient temperature. The resulting monoclinic blue solid was dissolved in THF (150 mL). The solution was then filtered through a plug of silica gel and rinsed with heptane:EtOAc (1:1). The volatiles were stripped under reduced pressure. The solid was rinsed with some toluene and dried in a 50° C. vacuum oven with nitrogen sweep. XRF analysis of the solid revealed 1,000 ppm ruthenium contamination. After multiple passes through silica plugs and activated carbon, compound 5 was isolated as a light gray solid (1.81 g, 2.65% yield). XRF analysis=95 ppm ruthenium. Tm=129.13° C. $^1$H NMR (500 MHz, CDCl3) δ 7.46 (bs, 2H), 7.09 (m, 4H), 6.88 (m, 4H), 6.77 (m, 4H), 6.60 (m, 2H), 6.53 (m, 4H), 5.23 (at, J=5.5 Hz, 2H), 2.97 (m, 4H), 1.56 (m, 4H), 1.43-1.28 (m, 8H).

EXAMPLE 11

Preparation of Precursor (N,N,N,N)-N,N'-(1,4-phenylenebis(methanylylidene))bis(N-phenylbenzene-1,4-diamine)

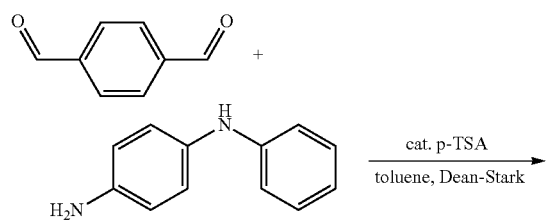

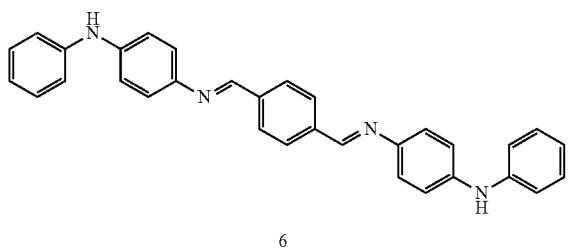

6

Terephthalaldehyde (10.0 g, 74.6 mmol), 4-ADPA (32.9 g, 178 mmol), and p-TSA (709 mg, 3.73 mmol) were transferred to a 3-necked 500 mL round-bottom flask equipped with a magnetic stir bar and thermocouple. Toluene (298 mL) was added. A Dean-Stark with condenser was placed on the flask, and the mixture was heated to reflux. After 10 hours, ca. 3 mL of water had collected. The mixture was cooled to ambient temperature. The resulting green solid was filtered and then rinsed with some toluene followed by heptane. Compound 6 was isolated as a crystalline green solid after drying in a 50° C. vacuum oven with nitrogen sweep (34.8 g, Quant.). $^1$H NMR (500 MHz, DMSO-d6) δ 8.74 (s, 2H), 8.35 (bs, 2H), 8.03 (s, 4H), 7.35 (m, 4H), 7.27 (m, 4H), 7.13 (m, 8H), 6.87 (m, 2H).

EXAMPLE 12

Preparation of N,N'-(1,4-phenylenebis(methylene))bis(N-phenylbenzene-1,4-diamine)

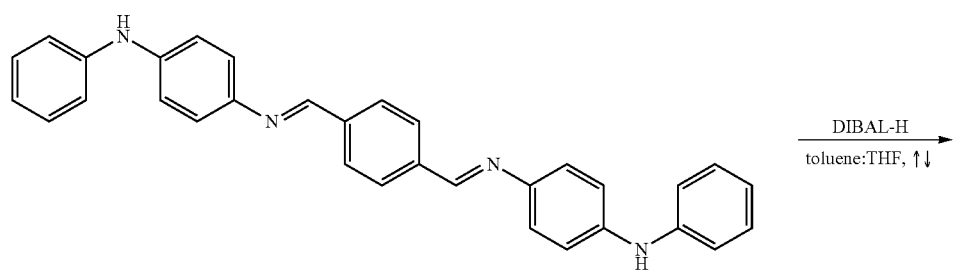

6

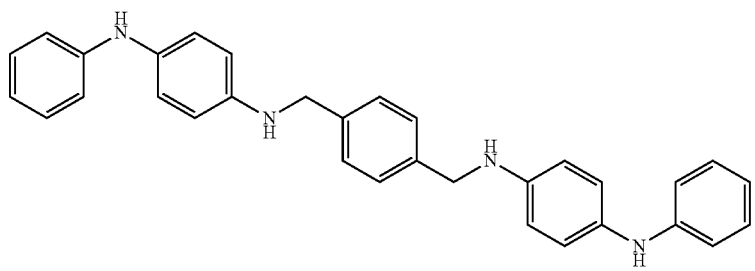

7

DIBAL-H (101 g, 25 wt. % in toluene) was slowly cannulated into a 1 L round-bottom flask that contained THF (86 mL). Then the di-imine 6 (20.0 g, 42.9 mmol) was carefully added at ambient temperature. After the addition was complete, the mixture was heated to 60° C. and allowed to react for 19 hours (after 3 hours of reaction time, additional DIBAL-H (20.0 g, 25 wt. % in toluene) was added). Then the reaction was cooled using an ice-water bath to ca. 5-10° C., at which point a saturated solution of NaK tartrate was added drop wise until the reaction mixture formed a gel. At that point, 275 mL of the NaK tartrate solution was quickly added, followed by 500 mL of EtOAc. The biphasic mixture was vigorously stirred overnight. The mixture was then transferred to a 1-L separatory funnel, and the layers were then separated. The organics (along with some suspended solids) were then washed with 10% NaOH (250 mL). The combined aqueous components were extracted with EtOAc (400 mL). The organics were combined and washed with water (200 mL). The organics were dried with Na$_2$SO$_4$. The mixture was then filtered, and the volatiles were removed under reduced pressure. The solids were washed with 10% NaOH (125 mL), followed by water. The solids were then placed in a flask with a stir bar and vigorously stirred with additional water. After filtration, the solids were then vigorously stirred in heptane (200 mL). The solids were filtered and washed with some additional heptane. The light-gray solid was placed in a 45° C. vacuum oven with nitrogen sweep (17.45 g of isolated product). ICP analysis: 397 ppm aluminum. The solids were re-dissolved in EtOAc:THF (1:1). The mixture was passed through a short plug of silica gel. The plug was rinsed with additional EtOAc:THF. The volatiles were then removed under reduced pressure. The solids were collected by filtration, using heptane to aid in removal from the flask. After drying in a vacuum oven overnight (15.2 g, 75% yield), the solid was re-analyzed using ICP. ICP analysis: 13 ppm aluminum. Tm=165.34° C. $^1$H NMR (500 MHz, DMSO-d6) δ 7.47 (bs, 2H), 7.33 (s, 4H), 7.08 (m, 4H), 6.85 (m, 4H), 6.79 (m, 4H), 6.77 (m, 4H), 6.59 (m, 2H), 6.55 (m, 4H), 5.91 (at, J=5.0 Hz, 2H), 4.21 (d, J=6.0 Hz, 4H).

EXAMPLE 13

Preparation of Precursor (N,N')-N,N'-(1,3-phenylenebis(methanylylidene))bis(N-phenylbenzene-1,4-diamine)

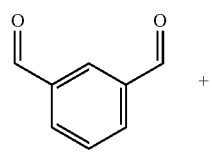

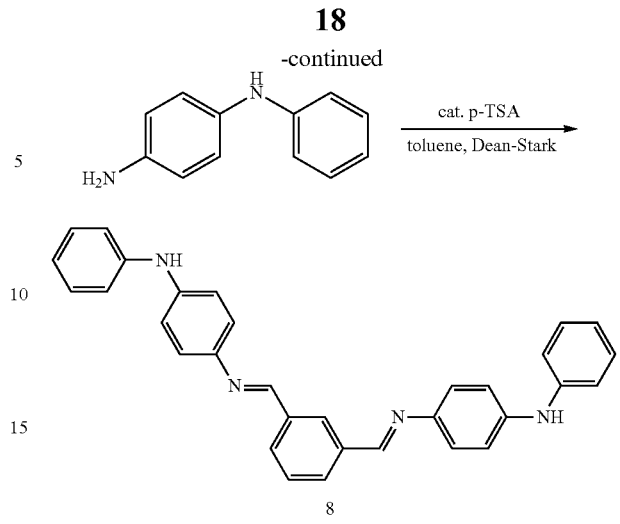

Isophthalaldehyde (10.0 g, 74.6 mmol), 4-ADPA (27.5 g, 149 mmol), and p-TSA (709 mg, 3.73 mmol) were transferred to a 3-necked 500 mL round-bottom flask equipped with a magnetic stir bar and thermocouple. Toluene (149 mL) was added. A Dean-Stark with condenser was placed on the flask, and the mixture was heated to reflux (a green solid precipitated during heat-up but re-dissolved upon further heating). After 2 hours, ca. 3 mL of water had collected. The mixture was cooled to ambient temperature. Heptane (300 mL) was added to the flask, and the contents were stirred for an additional 45 minutes. The solid was collected by filtration and subsequently washed with a saturated solution of NaHCO$_3$, EtOH, water, and then a final EtOH wash. After drying, the solid was triturated with toluene (400 mL) and then filtered once again. The resulting residue was rinsed with some EtOAc. The filtrate was concentrated under reduced pressure to reveal a yellow solid that was dried in a 50° C. vacuum oven with nitrogen sweep (24.7 g, 70.9% yield). $^1$H NMR (500 MHz, DMSO-d6) δ 8.77 (s, 2H), 8.47 (t, J=1.7 Hz, 1H), 8.32 (s, 2H), 8.02 (dd, J=1.6, 7.6 Hz, 2H), 7.64 (t, J=7.6 Hz, 1H), 7.34 (m, 4H), 7.27 (m, 4H), 7.13 (m, 8H), 6.86 (m, 2H).

EXAMPLE 14

Preparation of N,N'-(1,3-phenylenebis(methylene))bis(N-phenylbenzene-1,4-diamine)

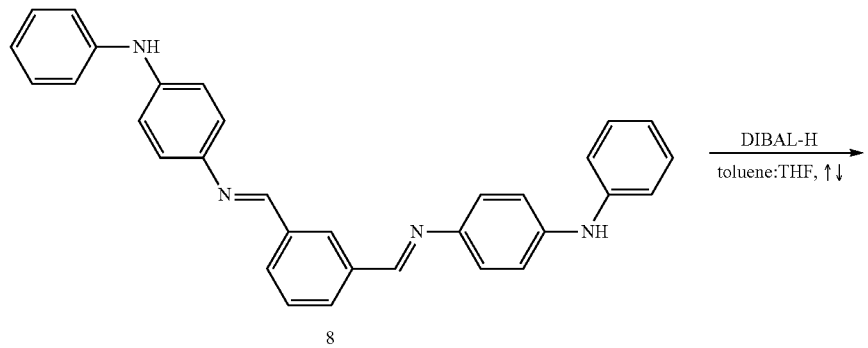

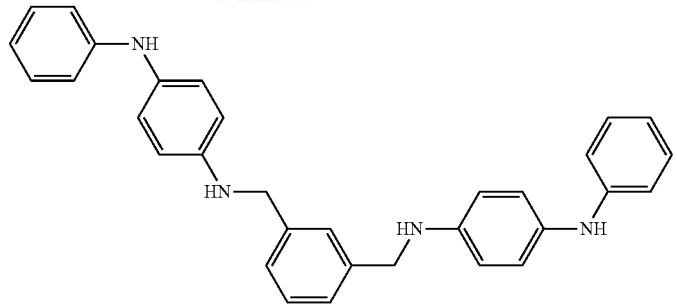

9

DIBAL-H (98.0 g, 25 wt. % in toluene) was slowly cannulated into a 1 L round-bottom flask that contained THF (106 mL). Then the di-imine 8 (24.7 g, 52.8 mmol) was carefully added at ambient temperature. After the addition was complete, the mixture was heated to 60° C. and allowed to react for 17.5 hours. Then the reaction was cooled using an ice-water bath to ca. 5-10° C., at which point a saturated solution of NaK tartrate was added drop wise until the reaction mixture formed a gel. At that point, 650 mL of the NaK tartrate solution was quickly added, followed by 500 mL of EtOAc. The biphasic mixture was vigorously stirred overnight. The mixture was then transferred to a 1-L separatory funnel, and the layers were then separated. The organics were dried with $Na_2SO_4$. The mixture was then filtered through a short plug of silica gel, and the cake was rinsed with a small amount of EtOAc and THF. The product was isolated as a light brown powder (21.5 g, 86% yield). Tm=103.92° C. $^1$H NMR (500 MHz, DMSO-d6) δ 7.47 (bs, 2H), 7.41 (t, J=1.6 Hz, 1H), 7.27 (m, 4H), 7.08 (m, 4H), 6.87 (m, 4H), 6.78 (m, 4H), 6.62-6.56 (m, 6H), 5.92 (t, J=6.0 Hz, 2H), 4.22 (d, J=6.0 Hz, 4H).

EXAMPLE 15

Preparation of Precursor (N,N',N,N')-N,N'-(1,4-phenylenebis(ethan-1-yl-1-ylidene))bis(N-phenyl-benzene-1,4-diamine)

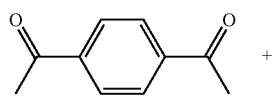

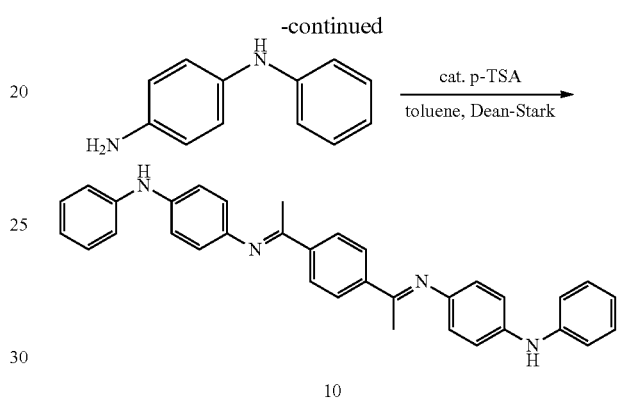

10

1,4-Diacetyl benzene (50.0 g, 310 mmol), 4-ADPA (128 g, 690 mmol), and p-TSA (4.37 g, 23.1 mmol) were transferred to a 4-necked 3 L round-bottom flask equipped with an overhead stirrer and thermocouple. Toluene (750 mL) was added. A Dean-Stark with condenser was placed on the flask, and the mixture was heated to reflux (a green solid precipitated during heat-up but re-dissolved upon further heating). After 7 hours, ca. 10 mL of water had collected. The mixture was cooled to ambient temperature. The solid was collected by filtration and subsequently washed with a saturated solution of $NaHCO_3$, water, and then EtOH. After drying in a 50° C. vacuum oven with nitrogen sweep, the product was isolated as a green crystalline solid (139.1 g, 91% yield). $^1$H NMR (500 MHz, CDCl3) δ 8.08 (bs, 6H), 7.23 (m, 4H), 7.12 (m, 4H), 7.06 (m, 4H), 6.80 (m, 6H), 2.33 (s, 6H).

EXAMPLE 16

Preparation of N,N'-(1,4-phenylenebis(ethane-1,1-diyl))bis(N-phenylbenzene-1,4-diamine)

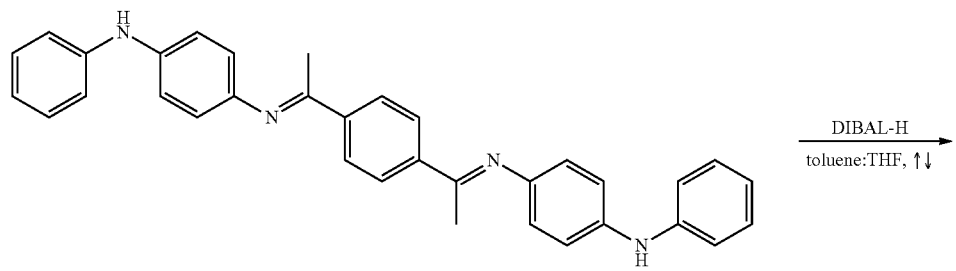

10

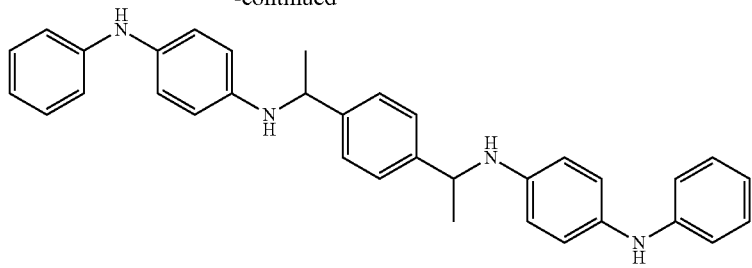

11

DIBAL-H (134 g, 25 wt. % in toluene) was slowly cannulated into a 1 L round-bottom flask. THF (81 mL) was then slowly added. Then the di-imine 10 (20.0 g, 40.4 mmol) was carefully added at ambient temperature. After the addition was complete, the mixture was heated to 60° C. and allowed to react for 25 hours. Then the reaction was cooled using an ice-water bath to ca. 5-10° C., at which point a saturated solution of NaK tartrate was added drop wise until the reaction mixture formed a gel. At that point, 500 mL of the NaK tartrate solution was quickly added, followed by 500 mL of EtOAc. The biphasic mixture was vigorously stirred overnight. The mixture was then transferred to a 1-L separatory funnel, and the layers were then separated. The organics were washed with a 10% NaOH solution (110 mL) and then water (200 mL×2). The organics were dried with $Na_2SO_4$. The mixture was then filtered. The solids were suspended in heptane (ca. 250 mL) and vigorously stirred. The solids were collected by filtration and then dried in a 50° C. vacuum oven with nitrogen sweep. The product was isolated as a tan powder (17.8 g, 88% yield). ICP analysis: 11 ppm aluminum. $^1$H NMR (500 MHz, DMSO-d6) δ 7.41 (d, J=4.0 Hz, 2H), 7.32 (bs, 4H), 7.06 (m, 4H), 6.80 (m, 4H), 6.74 (m, 4H), 6.58 (m, 2H), 6.48 (m, 4H), 5.81 (m, 2H), 4.39 (m, 2H), 1.39 (d, J=6.5 Hz, 6H).

EXAMPLE 17

Preparation of Precursor (N,N',N,N')-N,N'-(1,3-phenylenebis(ethan-1-yl-1-ylidene))bis(N-phenyl-benzene-1,4-diamine)

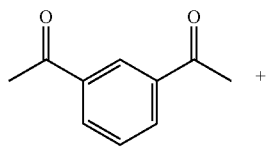 +

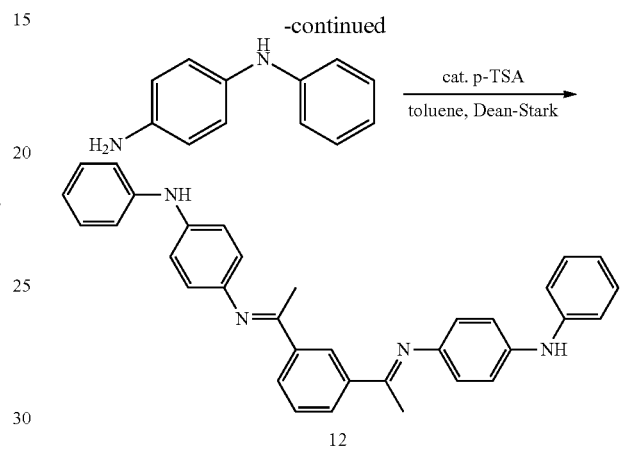

12

1,3-Diacetyl benzene (30.0 g, 185 mmol), 4-ADPA (77.0 g, 184 mmol), and p-TSA (2.62 g, 13.9 mmol) were transferred to a 4-necked 3-L round-bottom flask equipped with an overhead stirrer and thermocouple. Toluene (450 mL) was added. A Dean-Stark with condenser was placed on the flask, and the mixture was heated to reflux. After 8 hours, ca. 6.1 mL of water had collected. The mixture was cooled to ambient temperature. The solid was collected by filtration and subsequently washed with a saturated solution of $NaHCO_3$, water, and then EtOH. After drying in a 50° C. vacuum oven with nitrogen sweep, 12 was isolated as a green crystalline solid (41.0 g, 45% yield). $^1$H NMR (500 MHz, DMSO-d6) δ 8.59 (m, 2H), 8.10 (dd, J=1.8, 7.8 Hz, 2H), 8.07 (bs, 2H), 7.12 (m, 4H), 7.59 (t, J=8.0 Hz, 1H), 7.22 (m, 4H), 7.12 (m, 4H), 7.05 (m, 4H), 6.79 (m, 6H), 2.34 (s, 6H).

EXAMPLE 18

N,N'-(1,3-phenylenebis(ethane-1,1-diyl))bis(N-phenylbenzene-1,4-diamine)

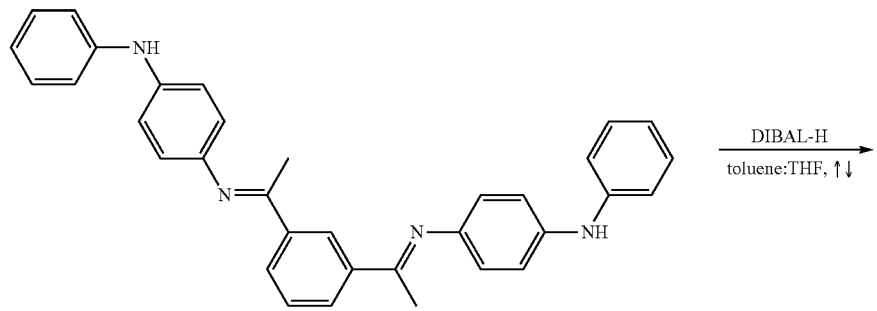

12

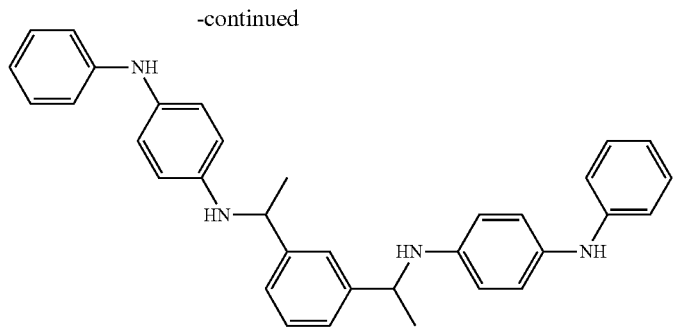

13

DIBAL-H (99.0 g, 25 wt. % in toluene) was slowly cannulated into a 1 L round-bottom flask containing THF (99.0 mL) that was cooled using an ice water bath. Then the di-imine 12 (24.5 g, 49.4 mmol) was carefully added at ambient temperature. After the addition was complete, the mixture was heated to 60° C. and allowed to react for 17.5 hours. Then the reaction was cooled using an ice-water bath to ca. 5-10° C., at which point a saturated solution of NaK tartrate was added drop wise until the reaction mixture formed a gel. At that point, 300 mL of the NaK tartrate solution was quickly added, followed by 300 mL of EtOAc. The biphasic mixture was vigorously stirred overnight. The mixture was then transferred to a 1-L separatory funnel, and the layers were then separated. The aqueous layer was extracted with additional EtOAc (250 mL). The organics were combined and dried with Na2SO4. After filtration, the volatiles were removed under reduced pressure. The solids were then dried in a 50° C. vacuum oven with nitrogen sweep. The product was isolated as a tan powder (18.7 g, 76% yield). $^1$H NMR (500 MHz, DMSO-d6) δ 7.41 (m, 2H), 7.37 (bs, 1H), 7.21 (m, 3H), 7.05 (m, 4H), 6.79 (m, 4H), 6.73 (m, 4H), 6.58 (m, 2H), 6.48 (m, 4H), 5.80 (m, 2H), 1.39 (at, J=6.5 Hz, 6H).

EXAMPLE 19

N-methylated mixture of N-phenyl-N-(1-(4-(1-((4-(phenylamino)phenyl)amino)ethyl)phenyl)ethyl)benzene-1,4-diamine

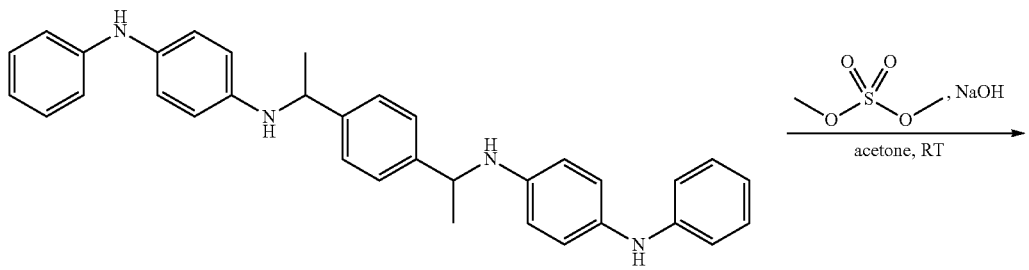

11

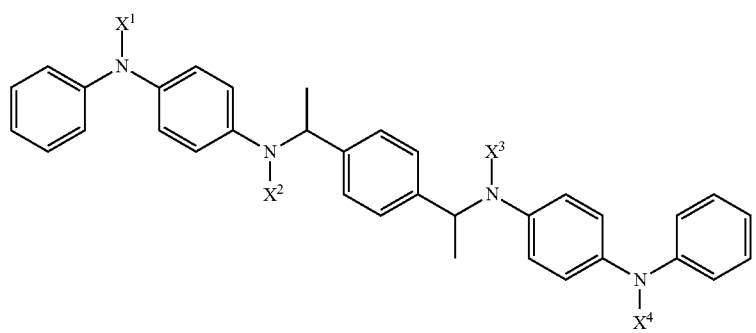

$X^1, X^2, X^3, X^4 = CH_3$ or H

14

As part of testing to confirm that methylated derivatives of Compound 11 are also effective antidegradants within the scope of the present invention, Compound 11 (51.2 g, 103 mmol) was placed in a 2-necked 1 L rb flask with overhead stirrer and then dissolved in acetone (0.50 M, 206 mL). Dimethyl sulfate (26.0 g, 206 mmol) was added all at once to the mixture. NaOH (10.34 g, 258 mmol) was dissolved in $H_2O$ (10.6 g) and then added all at once. The reaction was stirred for 24 hrs, and the volatiles were removed under reduced pressure. The brown residue was taken up in EtOAc (250 mL) and $H_2O$ (250 mL). The layers were separated. The aqueous component was extracted with additional EtOAc (100 mL). The organics were combined and dried with $MgSO_4$. After filtration, the volatiles were removed under reduced pressure to reveal the product as a light-brown solid (recovered 50.3 g). $^1H$ NMR indicated a mixture of compounds of the present invention wherein each compound is represented by formula identified above as "14".

The compounds of the present invention may also be synthesized by a catalytic reductive alkylation method from a polycarbonyl starting material and involving a heterogeneous transition metal catalyst in the presence of hydrogen. Examples of this method are provided below.

EXAMPLE 20

Preparation of N,N'-(1,4-phenylenebis(ethane-1,1-diyl))bis(N-phenylbenzene-1,4-diamine)

A mixture of 6.8 g. of 4-aminodiphenylamine (4-ADPA), 3.0 g. 1,4-diacetylbenzene, 75 ml. absolute ethanol, 0.6 g. sulfided 3% Pt/C catalyst and 1 g. of 1% phosphoric acid was charged to a 300 ml Parr autoclave. The system was purged three times with nitrogen by pressurizing to 100 psig and releasing. After the nitrogen purge, the system was heated to 150 C and then pressurized and maintained at 400 psig with hydrogen with agitation rate at 1800 rpm. The system was reacted for 120 minutes at which time no further hydrogen consumption could be detected.

The autoclave was cooled to room temperature and the mixture containing heavy white solids was analyzed. HPLC-MS analysis revealed complete conversion of 4-ADPA. The white solids were revealed by the same analysis to be the desired product N,N'-(1,4-phenylenebis(ethane-1,1-diyl))bis(N-phenylbenzene-1,4-diamine).

EXAMPLE 21

Preparation of N,N'-(1,3-phenylenebis(ethane-1,1-diyl))bis(N-phenylbenzene-1,4-diamine)

A mixture of 6.8 g. of 4-aminodiphenylamine (4-ADPA), 3.0 g. 1,3-diacetylbenzene, 75 ml. absolute ethanol, 0.6 g. sulfided 3% Pt/C catalyst and 1 g. of 1% phosphoric acid was charged to a 300 ml Parr autoclave. The system was purged three times with nitrogen by pressurizing to 100 psig and releasing. After the nitrogen purge, the system was heated to 150C and then pressurized and maintained at 400 psig with hydrogen with agitation rate at 1800 rpm. The system was reacted for 120 minutes at which time no further hydrogen consumption could be detected.

The autoclave was cooled to room temperature and the light brown solution was analyzed. HPLC-MS analysis of the solution revealed the desired product N,N'-(1,3-phenylenebis(ethane-1,1-diyl))bis(N-phenylbenzene-1,4-diamine) to be the major product and minor amounts of by-products resulting from addition of only one 4-ADPA molecule to the 1,3-diacetylbenzene.

In order to demonstrate the multiple efficacies of the compounds of present invention, analytical procedures to measure oxygen degradation inhibition, ozone degradation inhibition and fatigue and crack propagation inhibition were performed. To demonstrate antioxidant efficacy, the oxidative induction time (OIT) of selected examples were evaluated. OIT is measured according to a procedure carried out in a differential scanning calorimeter (DSC) and is used by those of ordinary skill in the art to predict thermo-oxidative performance of a material. In this procedure, samples held in a sample cell and heated under a nitrogen atmosphere to a preselected temperature (for the present application 150° C.). Oxygen is then introduced to the sample cell and the length of time before the onset of degradation, as seen by the initiation of an endothermic process in the DSC trace, is measured. [N-(1,3-Dimethylbutyl)-N'-phenyl-p-phenylenediamine (6PPD) and N-(1,4-dimethylpentyl)-N'-phenyl-p-phenylenediamine (7PPD), known antidegradant additives for rubber that are commercially available from Eastman Chemical Company under the trademark Santoflex®, were also tested as controls for OIT. The results are listed in the following table:

TABLE 1

Oxidative Induction Time (OIT) measured at 150° C.

| Example | OIT at 150° C. (minutes) |
| --- | --- |
| no additive | 4 |
| 6-PPD (control) | 37 |
| 7-PPD (control) | 66 |
| 2 | 212 |
| 4 | 334 |
| 5 | 383 |
| 7 | 475 |
| 9 | 470 |
| 11 | 620 |
| 13 | 584 |
| 14 | 535 |

As indicated by the above data, the compounds of the present invention demonstrate surprisingly excellent antioxidant performance that compares well to 6PPD and 7PPD and indicates utility in fuels, lubes, tires and other applications that can benefit from a highly active antioxidant compound).

To demonstrate antiozonant efficacy, thin film ozonolysis of liquid nitrile rubber containing of selected examples of the compounds of the present invention was performed using a modified infrared spectroscopic technique. Liquid nitrile rubber was chosen as the substrate for ozonolysis studies as the nitrile group has an unperturbed infrared absorbance at 2237 $cm^{-1}$ that serves as a convenient internal reference to monitor the extent of the ozonolysis reaction. Extent of the reaction was followed by the increase in ratio of the carbonyl absorbance peak at 1725 $cm^{-1}$ to the reference peak at 2237 $cm^{-1}$.

To prepare samples for this analysis, liquid nitrile rubber (1312LV, Zeon Chemicals L.P., Louisville, Ky.) was dissolved into THF to make a 10% solution. For the samples in Table 2 below, the antidegradants formed in examples 2 and 11 were each added to separate amounts of liquid nitrile rubber solution such that the samples each contained 1 weight % concentrations of antidegradant based on the weight of nitrile rubber. 600 microliters of each antidegradant-containing composition was placed on a ZnSe horizontal attenuated total reflectance crystal trough plate (HATR) and dried under a stream of nitrogen to create a thin film of each composition for testing. A control sample using commercially available 6PPD antidegradant was also formed by (i) creating a composition containing 6PPD antidegradant in the liquid nitrile rubber 10% solution with 6PPD in an amount of 1% by weight based on the weight of nitrile rubber and (ii) forming a thin film of the control composition as described above.

Each thin film sample was then subjected to ozonolysis in a polystyrene chamber kept thermally equilibrated at 40° C. in a Shel Lab Model CE5F oven (Shel Lab, Cornelius, Oreg.) with ozone generated using a A2Z Ozone Inc. (Louisville, Ky.) model MP-1000 ozone generator. The ozonolysis reaction was allowed to proceed for 100 minutes under an ozone concentration of approximately 5 ppm. The infrared spectra were recorded using a Perkin-Elmer Spectrum-2 spectrophotometer. The extent of ozonolysis reaction relative to 6PPD was determined as the ratio of the 1725 cm$^{-1}$/2237 cm$^{-1}$ absorbance ratio for the test materials divided by the ratio of the 1725 cm$^{-1}$/2237 cm$^{-1}$ absorbance for 6PPD.

TABLE 2

| | Compound | Relative Extent of Ozonolysis |
|---|---|---|
| Control | 6PPD | 1.00 |
| 1 | Invention Ex. 2 | 0.43 |
| 2 | Invention Ex. 11 | 0.37 |

As demonstrated by the above data, the antidegradants of the present invention reduced the relative extent of ozonolysis after 100 minutes by about 60% as compared to 6PPD. The compounds of the present invention therefore are shown to demonstrate surprisingly excellent antiozonant performance that is superior to currently commercial antidegradants and indicates utility in applications that can benefit from a highly active antiozonant compound.

As noted above, improving the fatigue resistance of a rubber compound can dramatically improve performance of a rubber compound (such as tire rubber compounds) in service. Accordingly, efficacy of the compounds of the present invention as an antifatigue agent when used in the manufacture of vulcanized articles formed from vulcanizable elastomeric formulations of the present invention was determined according to the method described below.

As a preliminary step in the creation of test samples, antidegradant masterbatches of the compositions set forth in Table 3 below were prepared, with two items including compounds of the present invention as antidegradant (specifically the compounds of examples 2 and 11 above) one control item including conventional 6PPD antidegradant; and a second control including 4,4',4"-tris(1,3-dimethylbutylamino)triphenylamine (compound IV-a described in U.S. Pat. No. 8,833,417) as antidegradant. Masterbatches were prepared using a Kobelco Inc. 1.6 L banbury style mixer equipped with 4-wing H style rotors set to a rotor speed of 25 rpm. A DeltaTherm Delta T system Model AB431S temperature controller was used to control the mixer temperature to 80° C. Material weights in the proportions given in Table 3 were determined to fill 74% of the mixing chamber volume. Carbon black, ZnO, stearic acid, antidegradant and ⅓ of the rubber were added to the mixer and the ram was set to close the mixer, the start the mix time was taken when the ram was in the closed position. After 30 seconds of mixing, the ram was raised and ⅓ of the rubber was added, again the ram was set to close. After an additional 30 seconds of mixing after the ram closed, the final ⅓ of the rubber was added and the ram closed. The rotor speed was adjusted to 65 rpm and the ingredients were mixed until the mixer thermocouple sensor registered 170° C. The total time required for these steps was approximately 5 minutes. The temperature of the composition measured immediately after discharge was ~170° C.

The masterbatch preparations were allowed to rest overnight and then passed through the mixer again the next day in order to ensure that the carbon black was well dispersed. This "remill" step was performed in the same 1.6 L mixer, with the mixer control set to 80° C., and the rotor speed set to 65 rpm. The first pass mixture was added to the mixer, the ram closed. Mixing continued until the thermocouple sensor registered 157° C. The total time required for the remill step was approximately three and three quarter minutes. The temperature of the composition measured immediately after discharge was ~160° C.

TABLE 3

| Component | example 2 phr | example 11 phr | 6 PPD phr | U.S. Pat. No. 8,833,417 compound (IV-a) phr |
|---|---|---|---|---|
| Natural Rubber TSR-10 | 100 | 100 | 100 | 100 |
| N-330 Carbon Black | 50 | 50 | 50 | 50 |
| Zinc Oxide | 4.0 | 4.0 | 4.0 | 4.0 |
| Stearic Acid | 2.5 | 2.5 | 2.5 | 2.5 |
| Antidegradant | 2.0 | 2.0 | 2.0 | 2.0 |
| Total | 158.5 | 158.5 | 158.5 | 158.5 |

To form test samples of vulcanizable elastomeric formulations of the present invention (as well as a control vulcanizable elastomeric formulation), a conventional vulcanizing agent (polymeric sulfur) and a conventional vulcanization accelerator, N,N'-Dicyclohexyl-2-benzothiazole sulfonamide (DCBS), were blended into each of the preformed antidegradant containing rubber masterbatches set forth in Table 3 at concentrations set forth in Table 4 below.

TABLE 4

| | example 2 | example 11 | 6-PPD | U.S. Pat. No. 8,833,417 Compound (IV-a) |
|---|---|---|---|---|
| Table I Masterbatch | 156.5 | 156.5 | 156.5 | 156.5 |
| DCBS | 1 | 1 | 1 | 1 |
| Polymeric Sulfur | 4.0 | 4.0 | 4.0 | 4.0 |
| Total | 161.5 | 161.5 | 161.5 | 161.5 |

Mixing was performed using the same 1.6 L laboratory mixer, the temperature controller was set to 80° C. and the rotor speed was set to 35 rpm. Compositions were loaded into the mixer and the ram was set to close. After the ram was closed the batch was mixed for an addition 3 minutes. The total time required for the final mixing step was about three and three quarter minutes. The temperature of the vulcanizable elastomeric formulations as measured immediately after discharge was ~95° C.

To form vulcanized elastomeric article samples for testing, the vulcanizable elastomeric formulations were then sheeted on a two roll mill to a thickness of 2 to 3 millimeters. In accordance to ASTM D4482-11, sheets were cut, pressed and vulcanized in a mold for 60 minutes at 140° C. to form 6 test samples from each formulation. The vulcanized items were then aged for 25 days at 77° C. and 40% relative humidity. Subsequent to aging, the samples were tested at 100% strain in conformance to ASTM D4482-11. The relative aged fatigue performance is reported in Table 5 below as the ratio of average of six samples of the present invention to the average of 6 control samples of 6-PPD containing material.

TABLE 5

| Item number | Example 2 | Example 11 | 6-PPD | U.S. Pat. No. 8,833,417 Compound (IV-a) |
|---|---|---|---|---|
| Relative Aged Fatigue | 1.85 | 2.05 | 1.00 | 0.59 |

As indicated by the above data, the articles formed from vulcanizable elastomeric formulations of the present invention demonstrate surprisingly excellent resistance to fatigue and crack propagation that is markedly better than the articles formed using conventional 6PPD antidegradant. The compounds of the present invention accordingly impart highly desirable levels of anti-fatigue resistance and are therefore efficacious anti-fatigue agents.

In another aspect briefly referenced above, the present invention is directed to a composition that includes at least one compound of the present invention as described above. The specific amount of the compound of the present invention that is included in the composition may vary widely depending on the intended use application for the composition. It will be understood by one of ordinary skill in the art that the composition of the present invention can include one or more compounds of the present invention such that the concentration of each individual compound necessary to achieve the desired antidegradant efficacy is lower. Further, other known antidegradant additives may be included in the composition such that a reduced amount of the compound of the present invention may be required to achieve the total desired antidegradant efficacy.

In one embodiment that is exemplified in detail above, the composition of a present invention is a vulcanizable elastomeric formulation. The vulcanizable elastomeric formulation of the present invention includes at least one elastomer and the compound of the present invention. Preferably, the compound of the present invention is present in the vulcanizable elastomeric formulation in an amount of from 0.1 to 20.0 parts, preferably from 0.1 to 5.0 parts, per 100 parts elastomer.

The elastomer in the vulcanizable elastomeric formulation may be any vulcanizable unsaturated hydrocarbon elastomer known to one skilled in the art. These elastomers may include without limitation natural rubber or any synthetic rubber, for example diene containing elastomers such as polymers formed from butadiene; isoprene; or combinations of styrene and butadiene, or styrene and isoprene, or styrene, butadiene and isoprene; or polymers formed from ethylene, propylene and diene monomers such as ethylidene norbornadiene or 1,5-hexadiene. The vulcanizable elastomeric formulation may optionally also include other additives conventionally used in rubber processing, such as processing/flow aids, extenders, plasticizers, resins, adhesion promoters, bonding agents, buffers, fillers, pigments, activators, prevulcanization inhibitors, acid retarders, accelerators, fatty acids, zinc oxide, or other compounding ingredients or additives to further enhance the characteristics and/or improve the performance of the vulcanizable elastomeric formulation or the vulcanized elastomeric article from which it is formed Suitable accelerators may include, but not be limited to guanidines, thiazoles, sulfenamides, sulfenimides, dithiocarbamates, xanthates, thiurams, and combinations or mixtures thereof.

The vulcanizable elastomeric formulation of the present invention is useful in the manufacture of vulcanized elastomeric articles such as rubber belts and hoses, windshield wiper blades, vehicle tires and components thereof such as the tread, shoulder, sidewall and innerliner. Accordingly, in another aspect, the present invention is directed to a vulcanized elastomeric article with at least one component formed from the vulcanizable elastomeric formulation of the present invention. In one particular embodiment, the vulcanized elastomeric article is a vehicle tire and the tire component is a sidewall.

While the foregoing aspects of the present invention have described utilities primarily focused in the area of compositions related to vulcanized elastomeric article manufacture, it will be understood that the compound of the present invention may also be useful in compositions for other utilities where antioxidant and/or antiozonant efficacy is desired. According and as described above, the present invention in a general aspect is directed to a composition including the compound of the present invention. In one embodiment, the composition is an antidegradant composition with utility and efficacy for inhibition of degradation of a composition, formulation or article to which it is added or applied. The antidegradant composition of the present invention therefore includes the compound of the present invention and optionally a carrier for the compound. Suitable carriers are substantially inert with respect to the compound and include waxes, oils, or solids such as carbon black or silica.

In a separate embodiment, the composition of the present invention has a separate primary utility or functionality (such as a coating, lubricant, oil, fuel additive or fuel composition) and includes a functional ingredient and the compound of the present invention as a component. The functional ingredient is typically a degradable material such as a hydrocarbon but may also include other degradable materials. This embodiment therefore encompasses for example, a lubricant composition that includes a lubricant as the functional ingredient and the compound of the present invention. This embodiment further encompasses a combustible fuel composition that includes a combustible fuel as the functional ingredient and the compound of the present invention. This embodiment further encompasses a fuel additive composition that includes a fuel additive as the functional ingredient and the compound of the present invention.

A person skilled in the art will recognize that the measurements described herein are standard measurements that can be obtained by a variety of different test methods. The test methods described represents only one available method to obtain each of the required measurements.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of making an antidegradant compound, the method comprising:

reacting a p-phenylenediamine corresponding to formula IV:

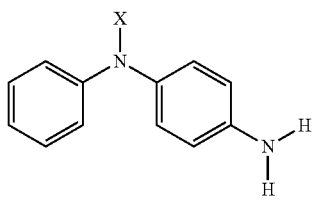

wherein X is selected from the group consisting of alkyl, aryl, alkylaryl groups and hydrogen;

with an alpha-hydroxy carbonyl compound corresponding to formula

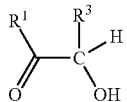

wherein $R^1$ and $R^3$ are each independently selected from the group consisting of alkyl, aryl, alkylaryl groups and hydrogen, and wherein $R^1$ and $R^3$ may optionally be bridged by a polymethylene group;

to thereby obtain an enediamine; and reducing the enediamine to thereby obtain a mixture comprising the antidegradant compound according to formula I:

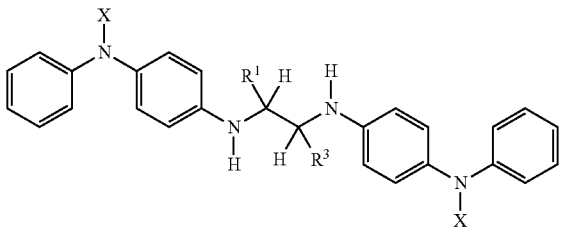

wherein X is each independently selected from the group consisting of alkyl, aryl, alkylaryi groups and hydrogen;

wherein $R^1$ and $R^3$ are each independently selected from the group consisting of alkyl, aryl, alkylaryl groups and hydrogen; and wherein $R^1$ and $R^3$ may optionally be bridged by a polymethylene group to form a cycloalkyl.

2. The method of claim 1, wherein the p-phenylenediamine comprises 4-aminodiphenvlamine.

3. The method of claim 1, wherein the alpha-hydroxy carbonyl comprises one or more of acetoin acetoin, acetol, and benzoin.

4. The method of claim 1, wherein the alpha-hydroxy carbonyl comprises acetoin, and wherein the p-phenylenediamine and the alpha-hydroxy carbonyl are reacted in the presence of a solvent and an acid catalyst.

5. The method of claim 4, wherein the acid catalyst comprises one or more of formic acid, acetic acid, propionic acid, p-toluenesulfonic acid, camphorsulfonic acid, hydrochloric acid, sulfuric acid, phosphoric acid, and a solid-supported acidic resin.

6. The method of claim 4, wherein the solvent comprises methylisobutylketone and the mixture comprising the antidegradant compound further comprises N-(1,3-Dimethylbutyl)-N'-phenyl-p-phenylenediamine.

7. The method of claim 4, wherein the solvent comprises acetone and the mixture comprising the antidegradant compound further comprises N-isopropyl-N'-phenyl-p-phenylenediamine.

8. The method of claim 1, wherein the enediamine is reduced by hydrogenation in the presence of: (a) a solvent, (b) a homogeneous or heterogeneous metal catalyst, and (c) one or more of hydrogen gas, formic acid, or a formic acid salt.

9. The method of claim 1, wherein the step of reacting the p-phenylenediamine with the alpha-hydroxy carbonyl and the step of reducing the enediamine thereby obtained are carried out in sequence, with optional isolation of the intermediate diimine compound.

10. The method of claim 1, wherein the step of reacting the p-phenylenediamine with the alpha-hydroxy carbonyl and the step of reducing the enediamine thereby obtained are carried out simultaneously in the same reaction mixture.

11. The method of claim 1, wherein the antidegradant compound comprises N,N'-(butane-2,3-diyl)bis(N-phenyl-benzene-1,4-diamine).

* * * * *